US009035098B2

(12) United States Patent
Feist et al.

(10) Patent No.: US 9,035,098 B2
(45) Date of Patent: May 19, 2015

(54) PROCESS FOR THE CONVERSION OF ALIPHATIC CYCLIC AMINES TO ALIPHATIC DIAMINES

(75) Inventors: Shawn D. Feist, Midland, MI (US); Daniel A. Hickman, Midland, MI (US); Erich J. Molitor, Midland, MI (US); David C. Molzahn, Midland, MI (US); Stacie Santhany, Auburn, MI (US); Abraham D. Schuitman, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/383,525

(22) PCT Filed: Jul. 30, 2010

(86) PCT No.: PCT/US2010/043878
§ 371 (c)(1),
(2), (4) Date: Jan. 11, 2012

(87) PCT Pub. No.: WO2011/014752
PCT Pub. Date: Feb. 3, 2011

(65) Prior Publication Data
US 2012/0116122 A1 May 10, 2012

Related U.S. Application Data

(60) Provisional application No. 61/230,335, filed on Jul. 31, 2009.

(51) Int. Cl.
*C07C 209/00* (2006.01)
*C07C 209/62* (2006.01)
*C07C 211/12* (2006.01)
*C07C 211/18* (2006.01)

(52) U.S. Cl.
CPC ............. *C07C 209/62* (2013.01); *C07C 211/12* (2013.01); *C07C 211/18* (2013.01); *C07C 2101/14* (2013.01)

(58) Field of Classification Search
None
See application file for complete search history.

(56) References Cited

U.S. PATENT DOCUMENTS

| 3,012,994 A | 12/1961 | Bell |
| 3,143,570 A | 8/1964 | Caldwell |
| 4,101,578 A | 7/1978 | Bock et al. |
| 4,602,091 A | 7/1986 | Brennan |
| 5,166,443 A | 11/1992 | Merger et al. |
| 5,371,293 A | 12/1994 | Takagawa |
| 5,608,113 A * | 3/1997 | Becker et al. ................. 564/480 |
| 5,789,620 A | 8/1998 | Waldmann et al. |
| 2002/0058654 A1* | 5/2002 | Coats et al. ............. 514/217.03 |
| 2012/0116123 A1 | 5/2012 | Santhany et al. |
| 2012/0123165 A1 | 5/2012 | Schuitman et al. |

FOREIGN PATENT DOCUMENTS

| DE | 74168 C | 9/1943 | |
| WO | 93/18017 A1 | 9/1993 | |
| WO | 0107382 | 2/2001 | |
| WO | 2007005594 | 1/2007 | |
| WO | WO2007005594 * | 1/2007 | ............ C07C 209/26 |
| WO | 2008/076795 A1 | 6/2008 | |

OTHER PUBLICATIONS

PCT/US2010/043878, International Search Report and Written Opinion.
PCT/US2010/043878, International Preliminary Report on Patentability.
Chinese Office Action dated Nov. 29, 2013; from Chinese counterpart Application No. 201080035250.9.
Instructions Chinese Office Action dated Jan. 10, 2014, from Chinese counterpart Application No. 201080035250.9.
EP Office Action dated Oct. 29, 2013; from EP counterpart Application No. 11712363.8.
Japanese Associate Office Ation dated Jul. 15, 2014; from JP counterpart Application No. 2012-523078.
Instructions to Japanese Office Action dated Aug. 18, 2014; from JP counterpart Application No. 2012-523078.
Response to Japanese Office Action dated Apr. 22, 2014 filed Aug. 22, 2014 for counterpart Japanese Application No. 2012-523078 and associate letter, 3 pages.

* cited by examiner

*Primary Examiner* — Clinton Brooks

(57) ABSTRACT

A process for conversion of aliphatic bicyclic amines to aliphatic diamines including contacting one or more bicyclic amines selected from the group consisting of 3-azabicyclo [3.3.1]nonane and azabicyclo[3.3.1]non-2-ene with ammonia and hydrogen, and alcohols in the presence of heterogeneous metal based catalyst systems, a metal selected from the group consisting of Co, Ni, Ru, Fe, Cu, Re, Pd, and their oxides at a temperature from 140° C. to 200° C. and a pressure from 1540 to 1735 psig for at least one hour reactor systems; forming a product mixture comprising aliphatic diamine(s), bicyclic amine(s), ammonia, hydrogen, and alcohol(s); removing said product mixture from the reactor system; removing at least some of the ammonia, hydrogen, water, alcohols, bicyclic amines from said product mixture; thereby separating the aliphatic diamines from said product mixture.

7 Claims, No Drawings

PROCESS FOR THE CONVERSION OF ALIPHATIC CYCLIC AMINES TO ALIPHATIC DIAMINES

CROSS-REFERENCE TO RELATED APPLICATIONS

This application is a non-provisional application claiming priority from the U.S. Provisional Patent Application No. 61/230,335, filed on Jul. 31, 2009, entitled "PROCESS FOR THE CONVERSION OF ALIPHATIC CYCLIC AMINES TO ALIPHATIC DIAMINES," the teachings of which are incorporated by reference herein, as if reproduced in full hereinbelow.

FIELD OF INVENTION

The instant invention relates to a process for the conversion of aliphatic cyclic amines to aliphatic diamines.

BACKGROUND OF THE INVENTION

The reductive amination of 1,3-cyclohexanedicarboxaldehyde or 1,3-cyanocyclohexanecarboxaldehyde produces a side product known as bicyclic amine or BA (3-azabicyclo[3.3.1]nonane). The formation of bicyclic amine contributes to lower yield of the desired 1,3-bis(aminomethyl)cyclohexane. Currently, there are not any meaningful means of conversion of such by-products to desired diamine products. Accordingly, there is a need for a process for the conversion of aliphatic cyclic amines to aliphatic diamines.

SUMMARY OF THE INVENTION

The instant invention provides a process for the conversion of aliphatic cyclic amines to aliphatic diamines.

In one embodiment, the instant invention provides a process for conversion of aliphatic cyclic amines to aliphatic diamines comprising the steps of: (1) selecting one or more cyclic amines; (2) contacting said one or more cyclic amines with ammonia and hydrogen, optionally water, and optionally one or more solvents in the presence of one or more heterogeneous metal based catalyst systems at a temperature in the range of from 120° C. to about 250° C. and a pressure in the range of from 700 to 3500 psig for a period in the range of at least one hour or more in one or more reactor systems; (3) forming a product mixture comprising one or more aliphatic diamines, optionally a portion of said one or more cyclic amines, optionally a portion of said ammonia, optionally a portion of said hydrogen, optionally water, and optionally a portion of said one or more solvents; (4) removing said product mixture from the reactor system; (5) removing at least a portion of said portion of ammonia, said portion of hydrogen, or mixture thereof from said product mixture via distillation; (6) removing at least a portion of said portion of water via distillation; (7) removing at least a portion of said portion of one or more optional solvents via distillation; (8) removing at least a portion of said portion of one or more cyclic amines; (9) thereby separating said one or more aliphatic diamines from said product mixture; and (10) thereby converting said one or more cyclic amines to one or more aliphatic diamines.

In an alternative embodiment, the instant invention further provides one or more aliphatic diamines produced according to the preceding process.

In an alternative embodiment, the instant invention provides a process for conversion of aliphatic cyclic amines to aliphatic diamines, in accordance with any of the preceding embodiments, except that the one or more cyclic amines is selected from the group consisting of 3-azabicyclo[3.3.1]nonane and azabicyclo[3.3.1]non-2-ene, and wherein the one or more aliphatic diamines comprises 1,3-bis(aminomethyl)cyclohexane.

In an alternative embodiment, the instant invention provides a process for conversion of aliphatic cyclic amines to aliphatic diamines, in accordance with any of the preceding embodiments, except that the one or more cyclic amines comprises hexahydro-1H-azepine, and wherein the one or more aliphatic diamines comprises hexamethylene diamine.

DETAILED DESCRIPTION OF THE INVENTION

The instant invention provides a process for the conversion of aliphatic cyclic amines to aliphatic diamines.

In one embodiment, the instant invention provides a process for conversion of aliphatic cyclic amines to aliphatic diamines comprising the steps of: (1) selecting one or more cyclic amines; (2) contacting said one or more cyclic amines with ammonia and hydrogen, optionally water, and optionally one or more solvents in the presence of one or more heterogeneous metal based catalyst systems at a temperature in the range of from 120° C. to about 250° C. and a pressure in the range of from 700 to 3500 psig for a period in the range of at least one hour or more in one or more reactor systems; (3) forming a product mixture comprising one or more aliphatic diamines, optionally a portion of said one or more cyclic amines, optionally a portion of said ammonia, optionally a portion of said hydrogen, optionally water, and optionally a portion of said one or more solvents; (4) removing said product mixture from the reactor system; (5) removing at least a portion of said portion of ammonia, said portion of hydrogen, or mixture thereof from said product mixture via distillation; (6) removing at least a portion of said portion of water via distillation; (7) removing at least a portion of said portion of one or more optional solvents via distillation; (8) removing at least a portion of said portion of one or more cyclic amines; (9) thereby separating said one or more aliphatic diamine from said product mixture; and (10) thereby converting said one or more cyclic amines to one or more aliphatic diamines.

In an alternative embodiment, the instant invention further provides one or more aliphatic diamines produced according to the preceding process.

In an alternative embodiment, the instant invention provides a process for conversion of aliphatic cyclic amines to aliphatic diamines, in accordance with any of the preceding embodiments, except that the one or more cyclic amines is selected from the group consisting of 3-azabicyclo[3.3.1]nonane and azabicyclo[3.3.1]non-2-ene, and wherein the one or more aliphatic diamines comprises 1,3-bis(aminomethyl)cyclohexane.

In an alternative embodiment, the instant invention provides a process for conversion of aliphatic cyclic amines to aliphatic diamines, in accordance with any of the preceding embodiments, except that the one or more cyclic amines comprises hexahydro-1H-azepine, and wherein the one or more aliphatic diamines comprises hexamethylene diamine.

According to the present invention one or more aliphatic cyclic amine by-products may be converted into a desired aliphatic diamine. In one embodiment, the one or more cyclic amines are selected from the group consisting of 3-azabicyclo[3.3.1]nonane and azabicyclo[3.3.1]non-2-ene. Such cyclic amines may be one or more by-products of reductive amination of one or more cycloaliphatic cyanoaldehydes as described in the U.S. provisional patent application with a Ser. No. 61/230,319, incorporated herein by reference in its entirety. In another embodiment, the one or more aliphatic cyclic amines comprise hexahydro-1H-azepine. In one embodiment, the one or more aliphatic diamines comprise 1,3-bis(aminomethyl)cyclohexane. In another embodiment, the one or more aliphatic diamines comprise hexamethylene diamine.

The one or more aliphatic cyclic amines is contacted with an amine, e.g. ammonia, methylamine, ethylamine, propylamine, or butylamine, and hydrogen, optionally water, and optionally one or more solvents, e.g. t-butanol or t-butylamine, in the presence of one or more heterogeneous metal based catalyst systems at a temperature in the range of from 130° C. to 300° C. and a pressure in the range of from 700 to 4000 psig for a period in the range of at least one hour or more in one or more batch or continuous reactor systems to form a product mixture. The one or more reactor systems comprise one or more continuous reactors, one or more batch reactors, or one or more semi-batch reactors, connected in series or in parallel. The ammonia may be present in mole equivalents in the range of from 2 to 100; for example, in the range of from 20 to 80. The reactor temperature may be in the range of from 130° C. to 300° C.; for example, 140° C. to 250° C.; or in the alternative, from 140° C. to 200° C. The reactor pressure may be in the range of from 700 to 4000 psig; for example, 700 to 3500 psig; or in the alternative, in the range of from 700 to 2000 psig. The hydrogen may have a partial pressure in the range of from 5 to 1000 psig; for example, from 100 to 1000 psig; or in the alternative, from 200 to 600 psig. The reactor may be a batch reactor or a continuous reactor. The one or more heterogeneous metal based catalyst systems may comprise a metal selected from the group consisting of Co, Ni, Ru, Fe, Cu, Re, Pd, oxides thereof, mixtures thereof, and combinations thereof. Such one or more heterogeneous metal based catalyst systems may comprise a bulk metal catalyst system, sponge-metal catalyst system, supported metal catalyst system, mixtures thereof, or combinations thereof. Such one or more heterogeneous metal based catalyst systems may comprise a bulk Co based catalyst system. The one or more heterogeneous metal based catalyst systems may further comprise one or more promoters or one or more binding agents or one or more catalyst supports. Such one or more promoters may be selected from the group consisting of alkali metals and alkaline earth metals. Such one or more binding agents may comprise silicon oxide, aluminum oxide, mixtures thereof, or combinations thereof. Such one or more catalyst supports may comprise silicon oxide, aluminum oxide, mixtures thereof, or combinations thereof. Such one or more heterogeneous metal based catalyst systems are commercially available as Raney Cobalt Catalyst from Grace Davison Catalyst Company, Co-0179T cobalt catalyst from BASF, and Co-138E catalyst from BASF. An amine such as ammonia is present in excess amount relative to the one or more aliphatic cyclic amines. An amine such as ammonia may, for example, be present in a range of 2 to 100 moles per mole of one or more aliphatic cyclic amines; or in the alternative, in a range of 10 to 90 moles per mole of one or more aliphatic cyclic amines; or in the alternative, in a range of 20 to 80 moles per mole of one or more aliphatic cyclic amines. Hydrogen may, for example, be present in a range of 0.1 to 30 moles per mole of one or more aliphatic cyclic amines; or in the alternative, in a range of 0.1 to 10 moles per mole of one or more aliphatic cyclic amines; or in the alternative, in a range of 0.1 to 6 moles per mole of one or more aliphatic cyclic amines.

The one or more heterogeneous metal based catalyst systems may be present in an amount necessary to catalyze the reaction between the one or more one or more aliphatic cyclic amines, hydrogen, and ammonia. The one or more heterogeneous metal based catalyst systems may, for example, comprise a fixed bed catalyst system.

A product mixture including one or more aliphatic diamines, optionally a portion of the one or more aliphatic cyclic amines, optionally a portion of the ammonia, optionally a portion of the hydrogen, optionally a portion of the water, and optionally a portion of the one or more solvents is formed in the one or more reactor systems, as described hereinabove. The product mixture is then removed from the one or more reactor systems and transferred to one or more distillation column arranged in sequential order. After the product mixture is transferred to one or more distillation columns arranged in sequential order, at least a portion of the ammonia, a portion of the hydrogen, or a mixture thereof is removed from the product mixture via one or more distillation steps. Subsequently, at least a portion of one or more solvents, if optionally present, and/or water is removed via one or more distillation steps. Subsequently, at least a portion of one or more aliphatic cyclic amines is removed via one or more distillation steps, thus separating the one or more aliphatic diamines from the product mixture and converting the one or more cyclic amines to one or more aliphatic diamines. The distillation process is further described in the U.S. provisional patent application with Ser. No. 61/230,300, incorporated herein by reference in its entirety.

The reaction between one or more aliphatic cyclic amines, hydrogen, and ammonia may optionally take place in the presence of one or more solvents, water, a mixture thereof, or a combination thereof. The feed into the reactor may comprise 0 to 90 percent by weight of one or more solvents, water, a mixture thereof, or a combination thereof, based on the weight of the feed, i.e. one or more aliphatic cyclic amines, hydrogen, and ammonia; or in the alternative, 0 to 30 percent by weight of one or more solvents, water, a mixture thereof, or a combination thereof, based on the weight of the feed; or in the alternative, 0 to 10 percent by weight of one or more solvents, water, a mixture thereof, or a combination thereof, based on the weight of the feed.

The reaction between one or more aliphatic cyclic amines, hydrogen, and ammonia may take place in a continuous reactor system; or in the alternative, it may take place in a batch reactor system; or in the alternative, it may take place in a semi-batch reactor system. Such reactor systems are generally known to a person of ordinary skill in the art. The continuous reactor system or the batch reactor system or the semi-batch reactor system may comprise one or more reactors in series, in parallel, or combinations thereof.

The one or more aliphatic diamines produced according to the instant invention may comprise 1,3-bis(aminomethyl)cyclohexane or hexamethylene diamine.

The conversion of one or more cyclic amine by-products to one or more desired aliphatic diamines may, for example, be illustrated via the following schematic:

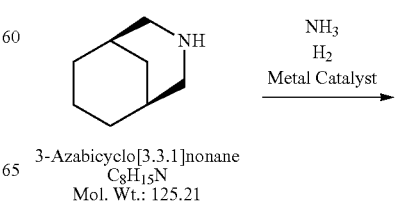

3-Azabicyclo[3.3.1]nonane
$C_8H_{15}N$
Mol. Wt.: 125.21

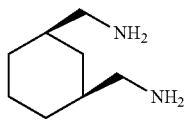

1,3 cis Bis(aminomethyl)cyclohexane
$C_8H_{18}N_2$
Mol. Wt.: 142.24

In the alternative, conversion of one or more cyclic amine by-products to one or more desired aliphatic diamines may, for example, be illustrated via the following schematic:

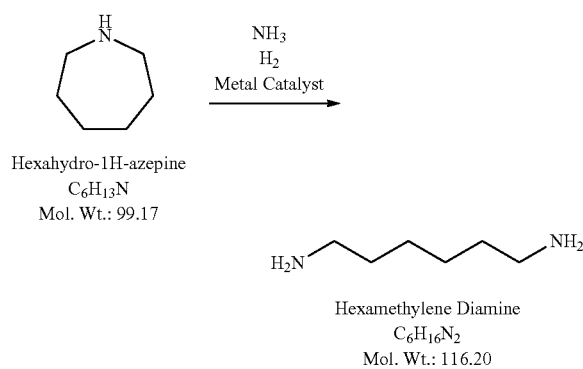

Hexahydro-1H-azepine
$C_6H_{13}N$
Mol. Wt.: 99.17

Hexamethylene Diamine
$C_6H_{16}N_2$
Mol. Wt.: 116.20

The one or more aliphatic diamines produced according to the instant invention may be used as a precursor to an aliphatic diisocyanate (bis(isocyanatomethyl)cyclohexane), as a chain extender in certain polyurethanes systems, or as an epoxy curing agent.

EXAMPLES

The following examples illustrate the present invention but are not intended to limit the scope of the invention.

Inventive examples 1-5 were prepared according to following procedures.

Inventive Example 1

4.6 grams of bicyclic amine and 2.3 grams of BASF Co-138 catalyst were added to a 300 ml Autoclave Engineers reactor. The reactor was sealed, and 56 grams of anhydrous ammonia were loaded into the reactor. The reactor pressure was approximately 119 psig at 17° C. Hydrogen pressure was applied at approximately 506 psig. The reactor was agitated at approximately 1000 rpm and heated to approximately 140° C. for approximately 24 hours. The reactor pressure was approximately 1889 psig. The ammonia and hydrogen were vented to yield a product which contained approximately 89 mole percent starting material and 11 mole percent 1,3-cis-bis(aminomethyl)cyclohexane as determined by gas chromatography (GC) analysis. Table I further reports catalyst type, hydrogen pressure, solvent type, reactor temperature, amount of ammonia in mole equivalents, and conversion rate in percent.

Inventive Example 2

4.7 grams of bicyclic amine, and 9.5 grams of t-butanol, and 2.3 grams of BASF Co-138 catalyst were added to a 300 ml Autoclave Engineers reactor. The reactor was sealed, and 50.1 grams of anhydrous ammonia were loaded into the reactor. The reactor pressure was approximately 122 psig at 20° C. Hydrogen pressure was applied at approximately 502 psig. The reactor was agitated at approximately 1000 rpm and heated to approximately 140° C. for approximately 23 hours. The reactor pressure was approximately 1589 psig. The ammonia and hydrogen were vented to yield a product which contained approximately 84.4 mole percent starting material and 15.6 mole percent 1,3-cis-bis(aminomethyl)cyclohexane as determined by gas chromatography (GC) analysis. Table I further reports catalyst type, hydrogen pressure, solvent type, reactor temperature, amount of ammonia in mole equivalents, and conversion rate in percent.

Inventive Example 3

4.65 grams of bicyclic amine, and 9.5 grams of t-butanol, and 2.4 grams of BASF Co-179 catalyst were added to a 300 ml Autoclave Engineers reactor. The reactor was sealed, and 49.8 grams of anhydrous ammonia were loaded into the reactor. The reactor pressure was approximately 122 psig at 17° C. Hydrogen pressure was applied at approximately 614 psig. The reactor was agitated at approximately 1000 rpm and heated to approximately 140° C. for approximately 23 hours. The reactor pressure was approximately 1735 psig. The ammonia and hydrogen were vented to yield a product which contained approximately 92.2 mole percent starting material and 7.8 mole percent 1,3-cis-bis(aminomethyl)cyclohexane as determined by gas chromatography (GC) analysis. Table I further reports catalyst type, hydrogen pressure, solvent type, reactor temperature, amount of ammonia in mole equivalents, and conversion rate in percent.

Inventive Example 4

4.66 grams of bicyclic amine, and 9.5 grams of t-butanol, and 2.3 grams of BASF Co-138 catalyst were added to a 300 ml Autoclave Engineers reactor. The reactor was sealed, and 50.3 grams of anhydrous ammonia were loaded into the reactor. The reactor pressure was approximately 125 psig at 20° C. Hydrogen pressure was applied at approximately 327 psig. The reactor was agitated at approximately 1000 rpm and heated to approximately 140° C. for approximately 22 hours. The reactor pressure was approximately 1540 psig. The ammonia and hydrogen were vented to yield a product which contained approximately 87.6 mole percent starting material and 12.4 mole percent 1,3-cis-bis(aminomethyl)cyclohexane as determined by gas chromatography (GC) analysis. Table I further reports catalyst type, hydrogen pressure, solvent type, reactor temperature, amount of ammonia in mole equivalents, and conversion rate in percent.

Inventive Example 5

4.60 grams of bicyclic amine, and 9.6 grams of t-butanol, and 2.6 grams of BASF Co-138 catalyst were added to a 300 ml Autoclave reactor. The reactor was sealed, and 51.6 grams of anhydrous ammonia were loaded into the reactor. The reactor pressure was approximately 110 psig at 16° C. Hydrogen pressure was applied at approximately 825 psig. The reactor was agitated at approximately 1000 rpm and heated to approximately 140° C. for approximately 22 hours. The reactor pressure was approximately 1983 psig. The ammonia and hydrogen were vented to yield a product which contained approximately 92.3 mole percent starting material and 7.7 mole percent 1,3-cis-bis(aminomethyl)cyclohexane as determined by gas chromatography (GC) analysis. Table I further reports catalyst type, hydrogen pressure, solvent type, reactor temperature, amount of ammonia in mole equivalents, and conversion rate in percent.

Comparative Example A 4.7 grams of bicyclic amine, and 58.7 grams of t-butylamine, and 2.3 grams of BASF Co-138 catalyst were added to a 300 ml Autoclave Engineers reactor. No ammonia was loaded into the reactor. The reactor pressure was approximately 1 psig at 21° C. Hydrogen pressure was applied at approximately 483 psig. The reactor was agitated at approximately 1000 rpm and heated to approximately 140° C. for approximately 23 hours. The reactor pressure was approximately 686 psig. The hydrogen was vented to yield a product which contained approximately 100 weight percent starting material and no 1,3-cis-bis(aminomethyl)cyclohexane or any other diamine product as determined by gas chromatography (GC) analysis. Table I further reports catalyst type, hydrogen pressure, solvent type, reactor temperature, amount of ammonia in mole equivalents, and conversion rate in percent.

TABLE I

| Example No. | Catalyst Type | Hydrogen Pressure | Solvent Type | Reactor Temperature (° C.) | Ammonia (Mole Eq.) | Conversion (%) |
| --- | --- | --- | --- | --- | --- | --- |
| Inventive 1 | Co-138 | 500 | None | 140 | 88 | 11.0 |
| Inventive 2 | Co-138 | 500 | t-BuOH | 140 | 79 | 15.6 |
| Inventive 3 | Co-179 | 500 | t-BuOH | 140 | 79 | 7.8 |
| Inventive 4 | Co-138 | 200 | t-BuOH | 140 | 79 | 12.4 |
| Inventive 5 | Co-138 | 700 | t-BuOH | 140 | 83 | 7.7 |
| Comparative A | Co-138 | 500 | t-BuNH$_2$ | 140 | 0 | 0 |

The present invention may be embodied in other forms without departing from the spirit and the essential attributes thereof, and, accordingly, reference should be made to the appended claims, rather than to the foregoing specification, as indicating the scope of the invention.

We claim:

1. A process for conversion of aliphatic cyclic amines to aliphatic diamines comprising the steps of:
    selecting one or more bicyclic amines;
    contacting said one or more bicyclic amines selected from the group consisting of 3-azabicyclo[3.3.1]nonane and azabicyclo[3.3.1]non-2-ene with ammonia and hydrogen, optionally water, and optionally one or more alcohols in the presence of one or more heterogeneous metal based catalyst systems comprising a metal selected from the group consisting of Co, Ni, Ru, Fe, Cu, Re, Pd, oxides thereof, mixtures thereof, and combinations thereof at a temperature in the range of from 140° C. to about 250° C. and a pressure in the range of from 1540 to 1735 psig for a period in the range of at least one hour or more in one or more reactor systems, wherein the ammonia is present in in the range of from 79 to 88 mole equivalent;
    forming a product mixture comprising one or more aliphatic diamines, a portion of said one or more bicyclic amines, a portion of said ammonia, a portion of said hydrogen, optionally water, and a portion of said one or more solvents;
    removing said product mixture from the reactor system;
    removing at least a portion of said portion of ammonia, said portion of hydrogen, or mixture thereof from said product mixture via venting;
    removing at least a portion of said portion of water via distillation;
    removing at least a portion of said portion of one or more alcohols via distillation;
    removing at least a portion of said portion of one or more bicyclic amines;
    thereby separating said one or more aliphatic diamines from said product mixture; and
    thereby converting said one or more bicyclic amines selected from the group consisting of 3-azabicyclo[3.3.1]nonane and azabicyclo[3.3.1]non-2-ene to one or more aliphatic diamines selected from the group consisting of 1,3-bis(aminomethyl)cyclohexane and hexamethylene diamine.

2. The process of claim 1, wherein said one or more reactor systems comprise one or more continuous reactors, one or more batch reactors, or one or more semi-batch reactors, or combinations thereof in series, in parallel, or combinations thereof.

3. The process of claim 1, wherein said one or more heterogeneous metal based catalyst systems is a bulk metal catalyst system, sponge-metal catalyst system, supported metal catalyst system, mixtures thereof, or combinations thereof.

4. The process of claim 1, wherein said one or more heterogeneous metal based catalyst systems comprises a bulk Co based catalyst system.

5. The process of claim 1, wherein said one or more heterogeneous metal based catalyst systems further comprises one or more promoters or one or more binding agents.

6. The process of claim 5, wherein said one or more promoters are selected from the group consisting of alkali metals and alkaline earth metals.

7. The process of claim 5, wherein said one or more binding agents comprise silicon oxide, aluminum oxide, titanium oxide, zirconium oxide, mixtures thereof, or combinations thereof.

* * * * *